(12) United States Patent
Singh et al.

(10) Patent No.: US 6,531,115 B1
(45) Date of Patent: Mar. 11, 2003

(54) ANALGESIC AND REFRESHING HERBAL COMPOSITION AND A PROCESS FOR PREPARING THE SAME

(75) Inventors: Anil Kumar Singh, Lucknow (IN); Ratan Lal Bindra, Lucknow (IN); Rashmi Gupta, Lucknow (IN); Yogendra Nath Shukla, Lucknow (IN); Sushil Kumar, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/752,822

(22) Filed: Jan. 3, 2001

(51) Int. Cl.$^7$ .......................... A61K 7/26; A61K 35/78
(52) U.S. Cl. ........................ 424/58; 424/195.1
(58) Field of Search .......................... 424/49–58, 195.1

(56) References Cited

U.S. PATENT DOCUMENTS

| | | | | |
|---|---|---|---|---|
| 4,784,842 A | * | 11/1988 | London et al. | 424/45 |
| 4,879,106 A | * | 11/1989 | Voli | 424/54 |
| 5,043,153 A | * | 8/1991 | Videckl et al. | 424/49 |
| 5,149,521 A | * | 9/1992 | Hirose et al. | 424/58 |
| 5,472,684 A | * | 12/1995 | Nabi et al. | 424/49 |
| 6,248,309 B1 | * | 6/2001 | Iyer et al. | 424/49 |
| 6,264,926 B1 | * | 7/2001 | Farooqi et al. | 424/58 |
| 6,312,735 B1 | * | 11/2001 | Niazi et al. | 424/694 |

FOREIGN PATENT DOCUMENTS

| | | | |
|---|---|---|---|
| CA | 1133831 | * | 10/1982 |
| CH | 688787 | * | 3/1998 |
| CZ | 245 821 | * | 1/1986 |
| JP | 48015320 | * | 5/1973 |
| JP | 02138 115 | * | 5/1990 |
| JP | 06247864 | * | 9/1994 |
| JP | 08104615 | * | 4/1996 |
| JP | 09278666 | * | 10/1997 |
| JP | 10077495 | * | 3/1998 |
| KR | 9708151 | * | 5/1997 |
| RO | 76653 | * | 11/1981 |
| SU | 1223910 | * | 4/1986 |
| SU | 1782 589 | * | 12/1992 |
| WO | 9844901 | * | 10/1998 |

OTHER PUBLICATIONS

Farooqi et al (II) "Medicinal Plants in Oral Health Care in India" Jl. Medicinal & Aromatic Plant Sci. 20:441–450, 1998.*
Sushi Kumar et al "Plants Used Traditionally in the Care of the Tooth" CIMAP Medicinal Plants: 80–89, 1994.*
Martindale Extra Pharmacopoeia 28$^{th}$ 00, 1982.*
Rawat et al Biochem Syst. Ecol. 17(1): 35–38, 1989.*
Douglas Flavor Ind(2): 152–154, 1971.*
Sharma et al Indian Perfume 27(2): 91–93, 1983.*
Sharma et al Indian Perfum. 26(2–4): 134–137, 1982.*
Bradu et al Dev. Act. Source of Clove Oil from 'Clocimum' *Ocimum Gratissimum*, 1989.*
Androsova Tsitologiya 28(9):1031–1 Substitute Eugenol from " " for Clove Oil, 1986.*
Nair et al Ind. Perfum. 27(2):125 Clocimum–Substitute of Eugenol for Clove Oil, 1983.*
Subti et al Ind. Perfum 24(2): 66–71 *Ocimum Gratissimum* for Eugenol Oil, 1980.*
Nayak et al J. Ind. Chem. Soc 29:203–205 Eugenol 61% from Ocimum Gratis., 1952.*

* cited by examiner

*Primary Examiner*—Shep K. Rose
(74) *Attorney, Agent, or Firm*—Foley & Lardner

(57) ABSTRACT

The invention provides an analgesic and refreshing herbal composition useful as dentrifrices, said composition comprising 50–60% Wt. of betle extract (from Piper betle leaves); 40–50% Wt. of one or more group I essential oil selected from *Levender officinal*, Dementholised oil (ex-*Mentha arvensis*), Fennel oil and *Ocimum gratissimum*; 3.5–6% Wt. of one or more group II essential oils and their isolates selected from *Ocimum Sanctum*, Pulegone (ex *Mentha pulegonium*), Carvone (ex. Dill seed) and Menthol (ex. *Mentha arvensis*); 1–5% Wt. of one or more group III essential oils selected from Camphor, turpentine oil, Cedarwood oil and Safrole oil, along with 0.5–2% Wt. of Thymol and 0.25–1% Wt. of preservative/antioxidant, and a process for preparing the composition.

26 Claims, No Drawings

ANALGESIC AND REFRESHING HERBAL COMPOSITION AND A PROCESS FOR PREPARING THE SAME

FIELD OF THE INVENTION

The present invention relates to an analgesic and refreshing herbal composition useful dentrifrices and a process for the preparation of the same.

1. Background of the Invention

Toothache is very common in human being of all age groups of both sex. Dental caries are caused due to the combined action of lactic acid, proteolytic enzymes and bacteria present in the oral cavity. Deep cavity in tooth, as a result of inflammation of the pulp causes pulpits. The root end abscess occurs in a tooth that has a dead nerve. Inflammation and swelling of the gingiva produce a deeper crevice or trough leading to gingivals abscess a periodontal disease. The application of tooth paint to the affected part produces counter irritation and local anaesthetic action, which in turn stops feeling sensation of pain.

2. Prior Art Relating to the Invention

Various formulations of such preparations available in market have been published in Indian Pharmaceutical Guide (1994) 32nd Edition published by Pamposh Publication, New Delhi, India. In seven formulations/preparations essential oil or isolates have been used as the major ingredients. Dabur India Ltd. markets two preparations, one having clove oil while the other named "Dar-Dant" a mixture of phenol, camphor, menthol and ajowan oil. Baidyanath Ayurved Bhawan also has two preparations—"Dant Dard Ki Dawa" and "Denta Beshari". The first one has phenol, camphor, Thymol, chlorobutol (I.P.), clove oil and chloroform while the second one has tannic acid, phenol, clove oil, cinnam m oil and glycerol (I.P.). Dentacare by Kothari Laboratory have borax, methyl salicylate, clove oil, tannic acid, potassium iodide, camphor and phenol. Dentolin by Jupiter Pharmaceuticals Pvt. Ltd. have creosote oil, clove oil, tincture myrrh, tincture iodine, procaine H, camphor, glycerin and chloroform while Dentosol by Synthochem have camphor, menthol, Thymol and katha.

All these formulations contain essential oil or their isolates as their major ingredients. "Dar-Dant" (from Dabur India Ltd.) contains phenol IP 27.9% v/v, clove oil IP 18.6% v/v, Camphor IP 14.0% w/v, oil Menthol IP 18.6% v/v, Azowan oil (IP 66) 2.3% v/w, non aqueous base 100%. The oil preparation named "Clove oil" (from Dabur India Ltd.) contains 100% clove oil only. "Dant Dard ki Dawa" (from Baidyanath Ayurved Bhawan) contains phenols IP 1% w/v, Camphor (IP, 66) 5% w/v, Thymol IP 22.5% w/v, Chloro butanol IP 1% w/v, Clove oil IP 25% v/v, Chloroform Sp. IP q.s. Alcohol content 48–52% v/v. "Danta Beshari" (from Baidyanath Ayurved Bhawan) contains Tannic acid IP 10% w/v, Phenol IP 1% w/v, Clove oil IP 0.05% v/v, cinnamon oil (IP66) 0.25% v/v, glycerin IP 100% v/v.

Dantacare (from Kothari Laboratories) contains Borex 0.28%, Methyl salicylate 0.16%, clove oil 16%, Tannic acid 0.32%, potassium iodide 2.088%, Camphor 0.24%, Phenol 0.14%, Thymol 0.28%, chloroform 0.3%, Menthol 0.20%.

Each ml of Dantaolina (by Jupiter Pharmaceutical Ltd.) contains: Creosote 5%, Clove oil 5%, Tinct. Mayrrh 5%, Tinct. Iodine 25%. Procaine HCl 0.5%, Camphor 0.5%, Glycerolin 50%, Chloroform 30% and Dentosol (Prepared by Synthochem Pharmaceuticals) contains (in 5 ml) camphor 30 mg, menthol oil 0.1 ml, Thymol 30 ml, Clove oil 0.15 ml, Katha 50 mg, Syrup 4.57 ml.

All the above mentioned products have clove oil along with other ingredients like camphor, Thymol and menthol. In four preparations Dar-Dant, Denta care, Dant Dard Ki Dawa and Dentolin one or more synthetic chemicals have been used. While Denta Beshari of Baidyanath Ayurved Bhawan have cinnamom oil as one component, which possess cinnamaldehyde as major ingredient. Cinnamaldehyde is reported to produce dermatitis and have mutagenic activity. For pure natural formulation Dabur has utilized pure clove oil while Dentosol produced by Synthochem have Katha (Acacia catechu), which has not a agreeable taste and may not be liked by all. Moreover, most of these formulations contain phenol which is toxic in higher concentrations.

A histological study was carried out to determine whether zinc oxide oil of clove and zinc oxide eugenol preparation used to manage dental cavities near the pulp effect the cells when compared with healthy pulp; short term studies 2–3 days and long term studies 4–5 weekly, indicated no harmful effects from either materials. The paper titled "Effects on tooth pain zinc oxide clove oil or zinc oxide eugenol" by Guelzow, H. J. Struepig W. (A. V. Zahnerhaltungaskd. Uni. Hamburg zoo Hemburing Fed. Rep. Ger) Dtsch zahnacerth Z. 1981 368: 475–7 (Ger) (CA 95, 175745K) gives the result of the study. Although this paper indicates that zinc oxide clove oil and zinc oxide eugenol have no harmful effects, but there is no indication that pain due to dental caries get relieved by this formulation. Zinc oxide being an inert substance and generally used for coatings in cosmetics can't be of any help in relieving the pain due to dental caries.

Japanese Patent 9500,110,20 "Composition for oral cavity and periodontal diseases" by Nishida et al. describes a compound (dentrifrices) for oral cavity and periodontal diseases containing antibody (to cavity or periodontal diseases related microorganisms) selected from those present in blood, egg and milk, menthol, a flavor compound selected from carvone, anethol, cineole, methyl salicylate, geraniol, ethyl butyrate and cinnamaldehyde in the ratio 4:1 to 2:8 by Wt. The compound is excellent for antibody stability, can produce satisfactory antibody effect even after being stored for long time and gives comfortableness in its use. The use of anethol, cineol, menthol, ethyl tartarate and cinnamaldehyde in combination with antibodies of blood, egg and milk indicates its obviousness against antibodies to cavity periodental diseases related to microorganisms. The formation can't give instant relief to the aching tooth.

Phenol, camphor, clove oil, menthol and eucalyptus are dentist's remedies for pulpitis. Dentist also employ alcohol, Thymol, cinnamol oil and oil of winter-green as pain relievers during pulpitis. In a paper titled "The sedative action on toothache by reagents used on the Pulp" by Tutsumi Nagira and Torroyo Folia Pharmacol, Japan 9(4), 262–72 and ibid 12 (1), 82–88, 1930, the sedative effect produced by Phenol, camphor, clove oil menthol and eucalyptus in rabbits having artificial toothache was investigated. It was found that Phenol shows the strongest action, but it can cause oral irritation. Clove oil, menthol and eucalyptol are weak and camphor has no sedative effect. In another experiment in the same paper, the pain-relieving activity of alcohol, Thymol, cinnamol oil and oil of winter-green were investigated. It was found that pain-relieving activity of creosote was the most efficient, but creosote cannot be used as it is toxic and is generally used as disinfectant. Thymol, oil of winter-green and oil of cinnamon were very weak and alcohol has almost no effect.

OBJECTS OF THE INVENTION

The main object of this invention is to provide a process for the preparation of a composition of an herbal liquid dentrifrices for quick pain relief in the aching tooth.

Another object is to give a refreshing effect to the oral cavity after its application. Yet another object is to check the growth of bacteria in normal teeth.

DETAILED DESCRIPTION OF THE INVENTION

Accordingly, the present invention provides an analgesic, refreshing herbal composition useful as dentrifrices, said composition comprising 50–60% Wt. of betle extract (from Piper betle leaves); 40–50% Wt. of one or more group I essential oil selected from Levender officinal, Dementholised oil (ex-Mentha arvensis), Fennel oil and Ocimum gratissimum; 3.5–6% Wt. of one or more group II essential oils and their isolates selected from Ocimum Sanctum, Pulegone (ex Mentha pulegonium), Carvone (ex. Dill seed) and Menthol (ex. Mentha arvensis); 1–5% Wt. of one or more group III essential oils selected from Camphor, turpentine oil, Cedarwood oil and Safrole oil, along with 0.5–2% Wt. of Thymol and 0.25–1% Wt. of preservative/antioxidant.

The present invention also provides a process for preparing an analgesic, refreshing herbal composition useful as dentrifrices, said process comprising mixing 50–60% Wt. of betle extract (from Piper betle leaves); 40–50% Wt. of one or more group I essential oil selected from Levender officinal, Dementholised oil (ex-Mentha arvensis), Fennel oil and Ocimum gratissimum; 3.5–6% Wt. of one or more group II essential oils or their isolates selected from Ocimum Sanctum, Pulegone (ex Mentha pulegonium), Carvone (ex. Dill seed) and Menthol (ex. Mentha arvensis); 1–5% Wt. of one or more group III essential oils selected from Camphor, turpentine oil, Cedarwood oil and Safrole oil; with 0.5–2% Wt. of Thymol; heating the above mixture at a temperature in the range of 60–70° C. for a period in the range of ½ to 1 hour; Cooling it to ambient temperature and mixing 0.25–1% Wt. of preservative/antioxidant.

In an embodiment of the present invention, percentage of betle leaf extract present is between 50 to 55% by Wt.

In another embodiment of the present invention, percentage of group I essential oils present is between 40 to 45% by Wt.

In yet another embodiment of the present invention, percentage of group II essential oils and their isolates present is between 4 to 6% by Wt.

In still another embodiment of the present invention, percentage of group III essential oils present is between 2 to 3% by Wt.

In one another embodiment of the present invention, percentage of Thymol present is between 0.5 to 1% by Wt.

In one more embodiment of the present invention, the antioxidant used is α-tocopheryl acetate.

In yet another embodiment of the present invention, percentage of preservative/antioxidant present is between 0.25 to 0.5% by Wt.

In one another embodiment of the present invention, betle extract used may be extracted from betle leaves using solvent such as propylene glycol, absolute alcohol.

The aim of the present invention is to relieve the pain in the cavity of the teeth initiated at the gingival margine, where the teeth and the gum come together. The application of the composition to the effected part produces counter irritation and as pain depressant to the exposed nerves in the dental caries and is also an antiseptic. The presence of calcium, phosphorus, iron, nicotinic acid in the betle extract helps to bring the aching tooth to its normal condition. The extract of betle leaves helps as a depressant to the exposed nerves in the dental caries. Its antiseptic activity due to presence of vitamin C helps in relieving the pain.

The composition obits the drawbacks of known art. The sum total of properties of composition is entirely different from its individual components. The essential oils of Ocimum gratissimum, menthol, camphor and Thymol acts in synergy with the betle extracts and helps in reliving the pain immediately after its application. The different compositions have been described and which are illustrated by following examples and therefore, should not be construed to limit the scope of invention.

EXAMPLES

Example 1

| Ingredient | Amount | Percentage |
|---|---|---|
| Betle leaf extract (from Piper betle leaves in propylene glycol) | 225 ml | 50% |
| Essential oil of lavender officinalis | 188.75 ml | 41.95% |
| Essential oil of Ocimum sanctum | 22.5 g | 5.0% |
| Turpentine Oil | 11.25 ml | 2.5% |
| Thymol | 11.30 g | 0.30% |
| α- tocopheryl acetate (known antioxidant) | 1.25 g | 0.25% |

Commercial grade betle leaves (Piper betle Family—Piperaceae) of local origin from Uttar Pradesh, India (Deshi) after washing, cleaning were dried completely in shade. The leaves were powdered to 50 mesh. The powdered leaves were extracted with propylene glycol (Propane-1,2-diol) (Specification Wt. per ml 1.03, purity 97.0%, acidity alkalinity not more than 0.3 ml N/1% water 0.2%) or Absolute alcohol (Wt. per ml 0.750 g).

100 of powdered leaves were extracted with 300 ml of propylene glycol or absolute alcohol. After a contact time of 24 hour heating for 6 hour initially over a water bath and thereafter leaving in contact for 18 hour at ambient temperature. The volume of extract obtained was 225 ml. The powdered leaves were washed second time with 230 ml of propylene glycol which gave an extract of 220 ml after a contact time of 12 hour. This extract was used for extraction of fresh leaves for next batch.

Essential oil of Lavender officinalis and Ocimum sanctum is added to turpentine oil and mixed. Thymol is added and heated over a water bath at 50° C. till Thymol dissolves. To the betle extract prepared as described above this mixture is added slowly and mechanically stirred. It was allowed to settle down, filtered and α-Tocopheryl acetate (known antioxidant) is added.

This composition was tried on ten persons and it was observed that the effectiveness was not quick and instantaneous; it took about 40 min to relieve the pain and the relief was not complete.

Example 2

| Ingredient | Amount | Percentage |
| --- | --- | --- |
| Betle leaf extract (from Piper betle leaves in propylene glycol) | 225 ml | 50% |
| Dementholised Oil (DMO) (ex-*Mentha arvensis*) | 188.75 ml | 41.95% |
| Pulegone (ex-*Mentha plugium*) | 22.5 g | 5.0% |
| Cedarwood Oil | 11.25 ml | 2.5% |
| Thymol | 11.30 g | 0.30% |
| α- tocopheryl acetate (known antioxidant) | 1.25 g | 0.25% |

Dementholised oil (DMO) ex-*Mentha arvensis*, Pulegone (ex-*Mentha plugium* oil containing 90% Pulegone) and rectified Cedarwood oil were mixed together, at ambient temperature. Thymol was added and heated over a water bath at 60° C. The mixture was stirred and added to betle extract in propylene glycol prepared as discussed in experiment 1 at an temperature of 70° C. over a water bath. The composition was mechanically stirred and cooled to ambient temperature allowed to settle and filtered, α-tocopheorl acetate (known antioxidant) was added.

The application of this composition on aching tooth reduced the time of relief as compared to example 1 but the user did not appreciate the flavor.

Example 3

| Ingredient | Amount | Percentage |
| --- | --- | --- |
| Betle leaf extract (from Piper betle leaves in propylene glycol) | 225 ml | 50% |
| Fennel Oil | 188.75 ml | 41.95% |
| Carvone (ex Dill seeds) | 22.5 g | 5.0% |
| Safrole | 11.25 ml | 2.5% |
| Thymol | 11.30 g | 0.30% |
| α- tocopheryl acetate (known antioxidant) | 1.25 g | 0.25% |

Fennel oil, carvone (ex-Dill seeds) and Safrole were mixed together. To this mixture Thymol was added and heated over a water bath at 50° C. and mixed together. This composition was added to the betle leaf extract prepared as discussed in example No. 1. The composition was heated over a water bath, between a temperature of 60° C. and mechanically stirred. Cooled down to ambient temperature, settled and filtered; α-tocopheryl acetate (know antioxidant) was added.

On application of this composition to the aching tooth there is not much difference in relief of pain from the composition No. 1. It took about 40 min for relief of pain.

Example 4

| Ingredient | Amount | Percentage |
| --- | --- | --- |
| Betle leaf extract (from Piper betle leaves in propylene glycol) | 225 ml | 50% |
| Essential oil of *Ocimum gratissimum* | 188.75 ml | 41.95% |
| Menthol | 22.5 g | 5.0% |
| Camphor | 11.25 ml | 2.5% |
| Thymol | 11.30 g | 0.30% |
| α- tocopheryl acetate (known antioxidant) | 1.25 g | 0.25% |

Menthol (ex-*Mentha arvensis*) (purity 99.9%) was melted over a water bath at 50° C. with camphor and mixed. Essential oil from *Ocimum gratissimum* was added to it at ambient temperature and subsequently Thymol was added and mixed thoroughly.

The above mixture was added to betle extract in propylene glycol prepared as discussed in example 1 and heated over a water bath between a temperature of 60° C. and cooled. The composition was mechanically stirred at ambient temperature and allowed to settle, filtered and α-tocopheryl acetate (known antioxidant) was added.

The field trial of this composition was conducted in Lucknow (India) on fifteen human subjects between the age group of 6 to 60 years (eleven male and four female); amongst them seventy five percent reported relief in the pain within 20 min and twenty five percent reported relief within 30 min after first application of the composition. Sixty percent reported freshness in the mouth.

The composition of the present invention is not a mere admixtures resulting in near aggregation of properties of the individual ingredients but a synergistic mixture resulting in quick relief of toothache on its first application and refreshing of oral cavity. The synergistic activity is detailed in examples 1–4.

The Main Advantages of the Present Inventions are:
1. The pain in the tooth is relieved instantly without any toxic effect. The betle extract depresses the pain in the exposed nerve endings. The other micronutrients present in the extract bring the aching teeth back to the normal conditions.
2. The costly clove oil which is extracted from the flower buds of *Szygium aromaticum* has been completely replaced by a cheaper oil of *Ocimum gratissimum* commonly called Clocimum which is very easy to cultivate.
3. All the components used for preparation are derived from natural botanicals and are ecofriendly and agreeable to users.
4. All the plants are under cultivation in India and raw material is available in plenty.
5. *Ocimum gratissimum* oil in combination with menthol and camphor gives a pleasant odor and freshness to mouth.
6. When the solution is rubbed on the teeth by fingertip after the meal and rinsed with water it serves as mouthwash and provides freshness and good feeling to the oral cavity.
7. The composition does not contain any synthetic chemical ingredients. The essential oils used have antimicrobial activity. This preparation can even be used for normal teeth as a precaution to check the growth of bacteria.

What is claimed is:
1. An analgesic or toothache pain-relieving and substantially clove oil-free, refreshing herbal composition, said composition comprising:
50–60% Wt. of betle extract (from Piper betle leaves);
40–50% Wt. of one or more group I essential oils selected from *Levender officinal*, Dementholised oil (ex-*Mentha arvensis*, Fennel oil and *Ocimum gratissimum*:

3.5–6% Wt. of one or more group II essential oils and their isolates selected from *Ocimum Sanctum*, Pulegone (ex *Mentha pulegonium*), Carvone (ex. Dill seed) and Menthol (ex. *Mentha arvensis*);

1–5% Wt. of one or more group III essential oils selected from Camphor, turpentine oil, Cedarwood oil and Safrole oil, along with 0.3–2% Wt. of Thymol and 0–25% Wt. of preservative/antioxidant.

2. A composition as claimed in claim 1, wherein the percentage of betle leaf extract present is between 50 to 55% by Wt.

3. A composition as claimed in claim 1, wherein the percentage of group I essential oils present is between 40 to 45% by Wt.

4. A composition as claimed in claim 1, wherein the percentage of group II essential oils and their isolates present is between 4 to 6% by Wt.

5. A composition as claimed in claim 1, wherein the percentage of group III essential oils present is between 2 to 3% by Wt.

6. A composition as claimed in claim 1, wherein the percentage of Thymol present is between 0.5 to 1% by Wt.

7. A composition as claimed in claim 1, wherein the antioxidant is α-tocopheryl acetate.

8. A composition as claimed in claim 1, wherein the percentage of preservative/antioxidant present is between 0.25 to 0.5% by Wt.

9. A process for preparing an analgesic or toothache pain-relieving and substantially clove oil-free, refreshing herbal composition, said process comprising mixing 50–60% Wt. of betle extract (from Piper betle leaves);

40–50% Wt. of one or more group I essential oils selected from *Levender officinal*, Dementholised oil (ex-*Mentha arvensis*), Fennel oil and *Ocimum gratissimum*; 3.5–6% Wt. of one or more group it essential oils or their isolates selected from *Ocimum Sanctum*, Pulegone (ex *Mentha pulegonium*), Carvone (ex. Dill seed) and Menthol (ex. *Mentha arvensis*); 1–5% Wt. of one or more group III essential oils selected from Camphor, turpentine oil, Cedarwood oil and Safrole oil; with 0.3–2% Wt. of Thymol;

heating the above mixture at a temperature in the range of 60–70° C. for a period in the range of ½ to 1 hour;

Cooling it to ambient temperature and mixing 0.25–1% Wt. of preservative/antioxidant.

10. A process as claimed in claim 9, wherein Betle extract from Betle leaves is prepared using solvents such as propylene glycol or absolute alcohol.

11. A process as claimed in claim 9, wherein the percentage of betle leaf extract present is between 50 to 55% by Wt.

12. A process as claimed in claim 9, wherein the percentage of group I essential oils present is between 40 to 45% by Wt.

13. A process as claimed in claim 9, wherein the percentage of group II essential oils and their isolates present is between 4 to 6% by Wt.

14. A process as claimed in claim 9, wherein the percentage of group III essential oils present is between 2 to 3% by Wt.

15. A process as claimed in claim 9, wherein the percentage of Thymol present is between 0.5 to 1% by Wt.

16. A process as claimed in claim 9, wherein the antioxidant is α-tocopheryl acetate.

17. A process as claimed in claim 9, wherein the percentage of preservative/antioxidant present is between 0.25 to 0.5% by Wt.

18. An analgesic or toothache pain-relieving and substantially clove oil-free, refreshing herbal composition, comprising:

50–60% Wt. of betle extract (from Piper betle leaves);

40–50% Wt. of *Ocimum gratissimum*;

3.5–6% Wt. of Menthol (ex. *Mentha arvensis*);

1–5% Wt. of Camphor;

0.5–2% Wt. of Thymol; and 0.25–1% Wt. of preservative/antioxidant.

19. An analgesic, refreshing herbal composition as claimed in claim 18, wherein the antioxidant is α-tocopheryl acetate.

20. An analgesic, refreshing herbal composition as claimed in claim 18, wherein the Betle extract is a propylene glycol extract.

21. An analgesic, refreshing herbal composition as claimed in claim 18, which comprises about 50% Wt. of betle extract.

22. An analgesic, refreshing herbal composition as claimed in claim 18, which comprises about 41.95% Wt. of *Ocimum gratissimum*.

23. An analgesic, refreshing herbal composition as claimed in claim 18, which comprises about 5% Wt. of Menthol.

24. An analgesic, refreshing herbal composition as claimed in claim 18, which comprises about 2.5% Wt. of Camphor.

25. An analgesic, refreshing herbal composition as claimed in claim 18, which comprises about 3.0% Wt. of Thymol.

26. An analgesic or toothache pain-relieving and substantially clove oil-free, refreshing herbal composition, comprising:

about 50% Wt. of betle extract (from Piper betle leaves);

about 41.95% Wt. of *Ocimum gratissimum*;

about 5.0% Wt. of Menthol (ex. *Mentha arvensis*);

about 2.5% Wt. of Camphor;

about 3.0% Wt. of Thymol; and about 0.25% Wt. of preservative/antioxidant.

* * * * *